US012590050B2

(12) United States Patent
Tan et al.

(10) Patent No.: US 12,590,050 B2
(45) Date of Patent: Mar. 31, 2026

(54) PREPARATION METHOD OF BIOBASED ADIPIC ACID

(71) Applicant: Beijing University of Chemical Technology, Beijing (CN)

(72) Inventors: Tianwei Tan, Beijing (CN); Chun Shen, Beijing (CN); Xiao Liang, Beijing (CN)

(73) Assignee: Beijing University of Chemical Technology, Beijing (CN)

( * ) Notice: Subject to any disclaimer, the term of this patent is extended or adjusted under 35 U.S.C. 154(b) by 0 days.

(21) Appl. No.: 19/021,233

(22) Filed: Jan. 15, 2025

(65) Prior Publication Data

US 2025/0154091 A1     May 15, 2025

Related U.S. Application Data

(63) Continuation of application No. PCT/CN2024/144249, filed on Dec. 31, 2024.

(30) Foreign Application Priority Data

Jun. 6, 2024     (CN) .......................... 202410727318.3

(51) Int. Cl.
    *C07C 51/02*     (2006.01)
    *B01J 35/45*     (2024.01)
    (Continued)

(52) U.S. Cl.
    CPC .............. *C07C 51/02* (2013.01); *B01J 35/45* (2024.01); *B01J 35/613* (2024.01); *B01J 35/615* (2024.01);
    (Continued)

(58) Field of Classification Search
    CPC ........ B01J 35/45; B01J 35/615; B01J 35/613; B01J 37/0201; B01J 37/0236; B01J 37/04; B01J 37/08; B01J 37/343; C07C 2523/755
    See application file for complete search history.

(56) References Cited

U.S. PATENT DOCUMENTS

2008/0051601 A1     2/2008  Sawyer et al.
2016/0311746 A1 *  10/2016  Pinkos et al. ........... C07C 51/36
                                                              7/36

(Continued)

FOREIGN PATENT DOCUMENTS

CN         101816938 A     9/2010

OTHER PUBLICATIONS

Biomicrofluidics 2023, 17, 061503, pp. 1-20 (Cai et al.) (Year: 2023).*

(Continued)

*Primary Examiner* — Amy C Bonaparte
*Assistant Examiner* — Derek Rhoades
(74) *Attorney, Agent, or Firm* — Hemisphere Law, PLLC

(57) ABSTRACT

The present invention relates to a preparation method of biobased adipic acid. In the method, by using a nickel-based hydrogenation catalyst provided by the present invention, when a substrate concentration is as high as 200 g/L, the reaction of biobased sodium muconate and hydrogen is catalyzed in a batch reactor and a micro packed bed to prepare sodium adipate, and the yield of a target product is close to 100 mol %. Wherein the biobased sodium muconate is biobased sodium muconate obtained by microbial fermentation. The method has the advantages of short reaction path, good economy, and easy large-scale preparation, and lays a solid foundation for the industrialization of green synthesis of the biobased adipic acid.

3 Claims, 5 Drawing Sheets

(51) Int. Cl.

| | |
|---|---|
| *B01J 35/61* | (2024.01) |
| *B01J 37/02* | (2006.01) |
| *B01J 37/04* | (2006.01) |
| *B01J 37/08* | (2006.01) |
| *B01J 37/34* | (2006.01) |

(52) U.S. Cl.
CPC ....... *B01J 37/0201* (2013.01); *B01J 37/0236* (2013.01); *B01J 37/04* (2013.01); *B01J 37/08* (2013.01); *B01J 37/343* (2013.01); *C07C 2523/755* (2013.01)

(56) References Cited

U.S. PATENT DOCUMENTS

| | | |
|---|---|---|
| 2019/0382361 A1 | 12/2019 | Paul et al. |
| 2020/0308630 A1 | 10/2020 | Ellis et al. |

OTHER PUBLICATIONS

Ultrason. Sonochem. 2021, 73, 105490, pp. 1-16 (Lim et al.) (Year: 2021).*
J. Phys. Chem. B 1999, 103, 6171-6178 (Burattin et al.) (Year: 1999).*
Org. Process Res. Dev. 2021, 25, 2100-2109 and Supporting Information (Duan et al.) (Year: 2021).*
Chem. Eng. Sci. 2007, 62, 2663-2678 (Tadepalli et al.) (Year: 2007).*
Highly efficient catalysts for the synthesis of adipic acid from cis,cis-muconic acid, S. Scelfo et al., "Catalysis Communications", No. 84 vol., pp. 98-102 (Jun. 14, 2016).
CNIPA, Notification of First Office Action for Chinese application CN202410727318.3, Jul. 6, 2024.
CNIPA, Notification to grant patent right for Chinese application CN202410727318.3, Aug. 2, 2024.

* cited by examiner

Activation and
dissociation of
hydrogen

Chemical inertness, and high
thermal stability

● Nickel element

Carrier

Providing large specific surface area

PREPARATION METHOD OF BIOBASED ADIPIC ACID

TECHNICAL FIELD

The present invention belongs to the field of biobased chemicals, and relates to a catalytic preparation method of biobased adipic acid (AdA).

BACKGROUND

Adipic acid is a binary carboxylic acid containing 6 carbon atoms, and is widely used in the production of nylon 6.6, engineering plastics and degradable plastics such as PBAT. The Asia-Pacific region is not only the largest market for adipic acid, but will also be the fastest growing market for the need for adipic acid. The average annual growth rate of the use amount of adipic acid is about 5.3% from 2014 to 2020, and the global market capacity of adipic acid is 2.61 million tons in 2012. As of the end of December 2020, the global total production capacity of adipic acid is about 4.908 million tons. At present, adipic acid is generally produced through the petrochemical route. The traditional synthesis method of adipic acid is the cyclohexane oxidation technology that takes benzene as raw material, and the production capacity of adipic acid accounts for about 90% of the total world production capacity. After the reaction of the cyclohexane oxidation technology that takes benzene as the raw material, nitric acid is reduced to nitrogen oxide that causes great pollution. 10% of global man-made nitrogen pollution is discharged by adipic acid synthesis plants, which causes the greenhouse climate impact higher than $CO_2$ by 298 times. The use of green renewable raw material to produce biobased adipic acid can effectively reduce the caused environmental pollution. Nowadays, with the proposal of targets of peak carbon dioxide emissions and carbon neutrality, the traditional chemical synthesis technology of adipic acid is urgently to be eliminated, and the development of green production technologies of biobased adipic acid is extremely urgent, which is the focus of the academic and industrial circles all over the world.

At present, the main green synthesis technologies of adipic acid include: 1) total biosynthesis, including the methods, which have been proved to be feasible, reverse adipic acid degradation pathway, β-oxidation or reverse β-oxidation combined with ω-oxidation pathway, and 2-di-oxoheptanoic acid pathway; and 2) semi-biosynthesis in which precursors, such as cis,cis-muconic acid, etc. are obtained by biological fermentation and then converted into adipic acid by a chemical catalysis method. Because the related technology of biological fermentation for the preparation of muconic acid has been very mature, the concentration of the muconic acid product is superior than that of the former adipic acid from direct fermentation, so the latter is recognized as a more promising technology for industrialization.

The cis,cis-muconic acid (CCMA) is a diunsaturated dicarboxylic acid with six carbon atoms, and can be hydrogenated to adipic acid in a reducing atmosphere in the presence of a heterogeneous catalyst. A similar technique was first used in 1994 by Karen M. Draths and John W. Frost (Karen M. Draths, John W. Frost. Environmentally compatible synthesis of adipic acid from D-glucose[J]. Journal of the American Chemical Society, 1994, (116):399-400) for catalytic hydrogenation of about 2.5 g/L cis-muconic acid, and a yield of 90% was achieved under mild reaction conditions. At present, the existing relevant researches have mainly focused on the catalytic hydrogenation of muconic acid with precious metal (Pd, Pt, etc.) catalysts in organic solvents. For example, Draths and Niu et al. (W. Niu, K. M. Draths, J. W. Frost, Benzene-free synthesis of adipic acid, Biotechnology Progress. 18 (2002) 201-211) have researched the catalytic hydrogenation of muconic acid with Pt catalyst (10 wt %): The molar yield of adipic acid reaches 90%-97% after 2.5 hours. However, the substrate concentration is low (0.15 mol/L) and harsh operating conditions are used, such as $H_2$ pressure of 3.4 MPa. Thomas et al. (Raja R, Thomas J M, Xu M, et al. Highly efficient one-step conversion of cyclohexane to adipic acid using single-site heterogeneous catalysts[J]. Chemical Communications, 2006, (4): 448-450) also have obtained quantitative hydrogenation of muconic acid to adipic acid under high-pressure hydrogen condition (3 MPa). In addition, they have successfully tested some Ru bimetallic nanocatalysts loaded on mesoporous silica.

Although the existing literature on the hydrogenation of muconic acid to prepare adipic acid has obtained a high yield, there are still the following severe challenges: (1) precious metal (Pd, Pt, etc.) catalysts are mainly used, and the high price of precious metal is difficult to meet the principle of industrial economy; (2) the hydrogenation reaction takes organic solvents (ethanol, amyl alcohol, etc.) as the solvents, so the degree of green is insufficient; (3) the low substrate concentration, generally not more than 10 g/L, reduces the production intensity of a unit volume reactor, and the separation energy consumption is huge, which cannot be industrialized; (4) the existing literature completes the hydrogenation process (gas-liquid-solid three-phase reaction) in a stirring reactor, which brings the following problems: firstly, the gas-liquid dispersion mode is mechanical stirring, and the dispersion of gas is poor. The specific surface area of gas-liquid two-phase contact is only 200-2000 $m^2/m^3$, and the total volumetric gas-liquid mass-transfer coefficient is in the range of $1.27 \times 10^{-2}$-$15.40 \times 10^{-2}$ $s^{-1}$. Even under the high-speed stirring condition of 1000 rpm, the hydrogenation process still has the features of gas-liquid mass transfer control, which means that the interphase mass transfer behavior has a great influence on the apparent kinetics. Long reaction time is required (Yue Jun, Chen Guangwen, Yuan Quan, Luo Lingai, Gonthier Yves, Hydrodynamics and mass transfer characteristics in gas-liquid flow through a rectangular microchannel. Chemical Engineering Science, 2007, 62, 2096-2108; Yawalkar Archis A, Heesink Albertus B M, Versteeg Geert F, Pangarkar Vishwas G. Gas-Liquid Mass Transfer Coefficient in Stirred Tank Reactors. The Canadian Journal of Chemical Engineering, 2002, 80, 840-848). Secondly, hydrogen is one of the reactants. Hydrogen is flammable and explosive, and the explosion limit range is very wide, which aggravates the potential safety hazards of the process. Finally, the process cannot be operated continuously, which is not conducive to industrial production.

At present, the reaction substrate concentration is low; and the hydrogen pressure is high. It is difficult to achieve the industrial production of biobased adipic acid, which is still a technical problem that those skilled in the art have been trying to solve for a long time but cannot be solved.

SUMMARY

A first purpose of the present invention is to provide a nickel-based hydrogenation catalyst for preparing biobased adipic acid with respect to the problems of the prior art. The catalyst has the advantages of low cost, high catalytic activity and high selectivity compared with the traditional precious metal catalyst.

A second purpose of the present invention is to provide a preparation method of the nickel-based hydrogenation catalyst. The nickel-based hydrogenation catalyst prepared by the preparation method by controlling the reaction conditions has high catalytic activity and high selectivity, and the industrial production of biobased adipic acid with high substrate concentration (200 g/L) and high yield (100 mol %) can be realized.

A third purpose of the present invention is to provide a production method of biobased adipic acid, which replaces the traditional precious metal catalyst with an economical and cheap nickel-based hydrogenation catalyst, can efficiently realize the hydrogenation reaction in the preparation process of biobased adipic acid in either a batch stirring reactor or a self-designed reaction system with high efficiency, safety, continuous production and industrial value and can meet the requirements of large-scale production of biobased adipic acid.

Therefore, a first aspect of the present invention provides a nickel-based hydrogenation catalyst for preparing biobased adipic acid, which is composed of carrier loaded metal nickel.

In some embodiments of the present invention, the average particle size of the metal nickel is 2.5-4.5 nm, and the specific surface area of the nickel-based hydrogenation catalyst is 50-300 $m^2$/g.

In some embodiments of the present invention, the load of the metal nickel in the nickel-based hydrogenation catalyst is 2 wt % to 40 wt %.

A second aspect of the present invention provides a preparation method of the nickel-based hydrogenation catalyst, which comprises carrier pretreatment and metal nickel loading by a precipitation-deposition method, comprising:

step A: putting a carrier into a $Na_2CO_3$ aqueous solution for ultrasonic pretreatment; and after solid-liquid separation, drying the carrier to obtain a pretreated carrier;

step B: adding the pretreated carrier to water for ultrasonic treatment to obtain a carrier suspension;

step C: mixing a nickel source with urea and the water to obtain a nickel source-urea mixed solution;

step D: mixing the carrier suspension with the nickel source-urea mixed solution; sealing, stirring and impregnating; then unsealing, stirring and drying until the water completely volatilizes to obtain a dry nickel-based hydrogenation catalyst precursor;

step E: reducing the dry nickel-based hydrogenation catalyst precursor at high temperature in a hydrogen atmosphere to obtain a nickel-based hydrogenation catalyst.

In some embodiments of the present invention, the concentration of the $Na_2CO_3$ aqueous solution is 0.1-0.8 M, and a mass ratio of the $Na_2CO_3$ aqueous solution to the carrier is 5-15:1.

In some embodiments of the present invention, in step C, a molar ratio of the urea to the nickel source is 2-8.

In some embodiments of the present invention, in step C, a mass ratio of the nickel source to the water is 0.01-0.1.

In some embodiments of the present invention, in step D, a mass ratio of the pretreated carrier to the nickel source is 0.65-10.

In some embodiments of the present invention, the concentration of the carrier suspension is 20-100 g/L.

According to the present invention, in steps A and B, the ultrasonic time is 0-60 min.

In some embodiments of the present invention, in step D, the impregnation temperature is 30° C.-100° C.; and the impregnation time is 2-6 h.

In some embodiments of the present invention, in step D, the temperature of evaporation is 30-100° C.

In some embodiments of the present invention, in step E, the temperature of the high-temperature reduction is 300-1000° C.; and the time of the high-temperature reduction is 60-300 min.

A third aspect of the present invention provides a hydrogenation reaction system for preparing biobased adipic acid, which comprises a batch stirring reactor or a microreaction device.

According to the present invention, the microreaction device comprises a reaction liquid storage tank, a constant-flux pump, a micromixer, a micro packed bed reactor, a phase separator and a product collector connected successively; a hydrogen source is connected with the micromixer; a gas flow meter is arranged between the hydrogen source and the micromixer; and a back pressure valve is arranged on the phase separator.

In some embodiments of the present invention, the inner diameter of the micro packed bed reactor is 0.5-10 mm.

In some embodiments of the present invention, the length of the micro packed bed reactor is 2-20 cm.

A fourth aspect of the present invention provides a preparation method of the biobased adipic acid, which comprises conducting a hydrogenation reaction on biobased muconic acid or biobased sodium muconate for preparing adipic acid in the hydrogenation reaction system described in the third aspect of the present invention under the action of the nickel-based hydrogenation catalyst described in the first aspect of the present invention or the nickel-based hydrogenation catalyst prepared by the preparation method described in the second aspect of the present invention.

According to some embodiments of the present invention, when the hydrogenation reaction system comprises the batch stirring reactor, the preparation method of the biobased adipic acid comprises putting the nickel-based hydrogenation catalyst into the batch stirring reactor, adding a biobased muconic acid aqueous solution or a sodium muconate aqueous solution, and filling with hydrogen for a hydrogenation catalytic reaction to obtain adipic acid.

In some embodiments of the present invention, the concentration of the biobased muconic acid aqueous solution or the sodium muconate aqueous solution is ≥10 g/L when the batch stirring reactor is used for reaction.

In some embodiments of the present invention, a mass ratio of the biobased muconic acid or sodium muconate to the nickel-based hydrogenation catalyst is 1-50 when the batch stirring reactor is used for reaction.

According to the present invention, the pressure of hydrogen in the batch stirring reactor is 0.1-5 MPa.

In some embodiments of the present invention, the temperature of the hydrogenation reaction is 50-200° C. when the batch stirring reactor is used for reaction.

In some embodiments of the present invention, the time of the hydrogenation reaction is 5 min-24 h when the batch stirring reactor is used for reaction.

According to some embodiments of the present invention, when the hydrogenation reaction system comprises the microreaction device, the nickel-based hydrogenation catalyst is filled into the micro packed bed reactor; the muconic acid aqueous solution or the sodium muconate aqueous solution and hydrogen are injected into the micro packed bed reactor; and the micro packed bed reactor is heated in a water bath or an oil bath to conduct a catalytic hydrogenation reaction to obtain adipic acid.

According to the present invention, when the microreaction device is used for reaction, the nickel-based hydrogenation catalyst is filled into the micro packed bed reactor, including: a powdered nickel-based hydrogenation catalyst prepared by a powder carrier is firstly pressed, formed and sieved, and then filled into the micro packed bed reactor, or a spherical hydrogenation catalyst prepared by a spherical carrier is directly filled into the micro packed bed reactor.

In some embodiments of the present invention, the height of the filled catalyst bed is 2-15 cm when the microreaction device is used for reaction; and both ends of the filled catalyst bed are filled with inert glass beads.

In some embodiments of the present invention, the molar concentration of the biobased muconic acid aqueous solution or the sodium muconate aqueous solution is ≥10 g/L when the microreaction device is used for reaction.

In some embodiments of the present invention, the flow rate of the injected biobased muconic acid aqueous solution or the sodium muconate aqueous solution is 0.1-2 mL/min when the microreaction device is used for reaction.

In some embodiments of the present invention, when the microreaction device is used for reaction, the pressure of hydrogen injected into the micro packed bed reactor is 0.16-10.0 MPa; and the flow rate of the injected hydrogen is 10-100 mL/min.

In some embodiments of the present invention, the temperature of the hydrogenation reaction is 30-200° C. when the microreaction device is used for reaction.

In some embodiments of the present invention, the time of the hydrogenation reaction is 10 s-10 min when the microreaction device is used for reaction.

According to the present invention, the preparation method comprises: conducting a hydrogenation reaction of the muconic acid aqueous solution to obtain an adipic acid aqueous solution, and precipitating adipic acid solid by cooling; or, conducting a hydrogenation reaction of the sodium muconate aqueous solution to obtain a sodium adipate aqueous solution, dropwise adding inorganic acid for acidification, and then precipitating adipic acid solid by cooling.

The present invention is improved with respect to the disadvantage that the existing preparation technology of semi-biological adipic acid is difficult to achieve large-scale production, on the one hand, muconic acid is alkalized into sodium muconate; and on the other hand, a new preparation technology of the nickel-based catalyst is innovatively proposed and designed, which greatly improves the dispersion of active metal components in the catalyst, thereby improving the catalytic performance, making the industrialization of catalytic hydrogenation of the adipic acid possible with the low-price advantage, changing the cost problem caused by the long-term use of precious metal catalysts and greatly reducing the cost of industrial application. Through the above two strategies, a high target product yield with high substrate concentration is achieved, which lays a solid foundation for the industrial production of the biobased adipic acid.

The present invention first proposes and realizes the high-selectivity hydrogenation preparation of sodium adipate by using the self-made nickel-based catalyst to catalyze the biobased sodium muconate from a high concentration biomass source in the batch reactor and the micro packed bed. When the concentration is as high as 200 g/L, the yield of sodium adipate can reach 100 mol %, which is higher than the value reported in literature by nearly 20 times. The method has the advantages of short reaction path, simple operation, good economy, green and environmental protection, and easy large-scale preparation, provides advanced technical support for the industrial production of the biobased adipic acid, and has broad application prospects.

DESCRIPTION OF DRAWINGS

The present invention is further described in detail below in combination with the drawings.

DETAILED DESCRIPTION

In order to make the present invention easy to understand, the present invention will be described below in detail in combination with the drawings. However, before the present invention is described in detail, it should be understood that the present invention is not limited to specific embodiments of the description. The described embodiments are merely part of the embodiments of the present invention, not all of the embodiments. Based on the embodiments in the present invention, all other embodiments obtained by those ordinary skilled in the art without contributing creative labor will belong to the protection scope of the present invention. It should also be understood that the terms used herein are intended only to describe specific embodiments and do not indicate limitations.

Unless otherwise defined, all terms used herein have the same meanings as those generally understood by those ordinary skilled in the art to which the present invention belongs. Although any methods and materials similar or equivalent to the methods and materials described herein can also be used in the implementation or testing of the present invention, preferred methods and materials are now described.

I. Term

The term "biobased muconic acid" in the present invention is relative to the "muconic acid" prepared by the traditional biochemical method, and refers to the cis-muconic acid converted from biomass raw material in the present invention, or the cis-muconic acid prepared from the biomass raw material.

The term "preparation technology of semi-biological adipic acid" in the present invention means that the intermediate cis-biobased sodium muconate is firstly produced by biological fermentation, and then is converted into the second half of the chemical catalytic part in sodium adipate by a chemical catalytic method.

The term "biobased adipic acid" in the present invention refers to adipic acid converted from the biobased muconic acid.

Figure 3:
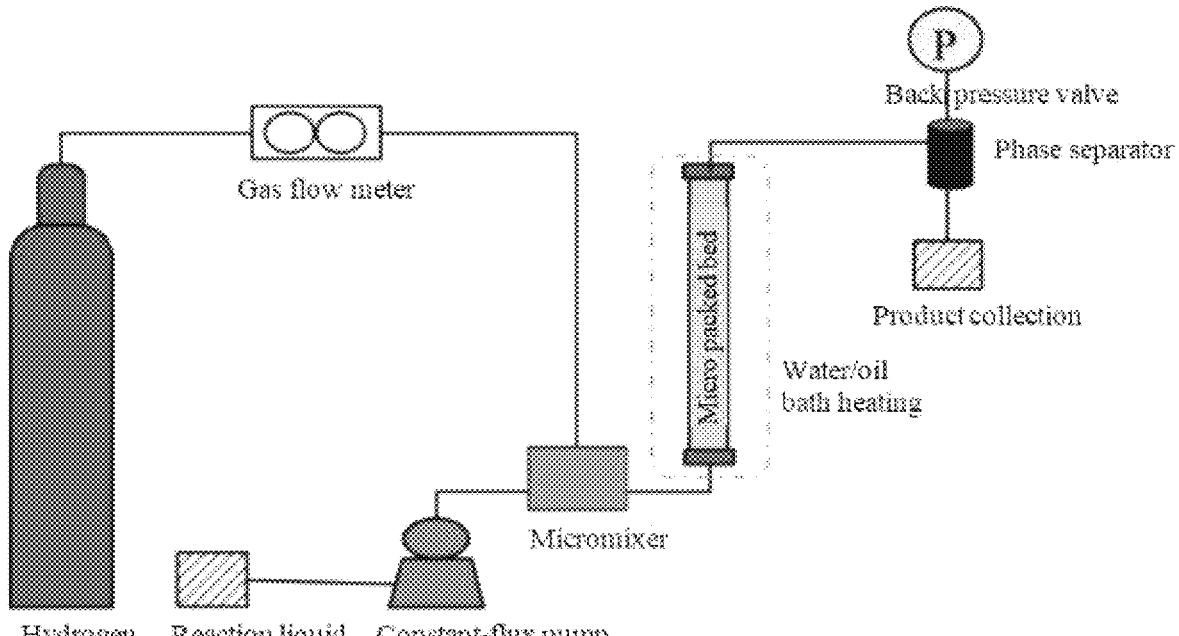
FIG. 3 shows a schematic diagram of a microreaction device in the present invention.

The term "micro packed bed" in the present invention refers to a microfluidic device composed of a 314L stainless steel pipe as a main body, and a microshunt, a micro packed bed and a micro phase separator self-designed and made, as shown in FIG. 3.

The term "nickel-based hydrogenation catalyst" in the present invention refers to a solid hydrogenation catalyst prepared by a precipitation-deposition method from a nickel source, alumina, SBA-15 and other carriers, wherein the "solid hydrogenation catalyst" refers to a solid substance that can change the chemical reaction rate (increase or decrease) of the reactants without changing chemical equilibrium in a chemical reaction, and has no change in own mass and chemical properties before and after the chemical reaction.

The term "water" in the present invention refers to deionized water, purified water, distilled water, etc. unless otherwise specified or limited.

II. Implementation Solution

Adipic acid, as an important bulk chemical, plays an important role in modern industry. With the proposal of targets of peak carbon dioxide emissions and carbon neutrality today, the traditional chemical synthesis technology of adipic acid has been in urgent need of elimination, while the existing new production technologies, such as full biological synthesis and semi-biological synthesis of adipic acid, are difficult to meet the requirements of industrialization. The inventor has found from the research that the industrialization of the full biological method is far away due to the need for gradual transformation of microorganisms, and the semi-biological chemical catalysis method is difficult to meet the requirements due to the expensive precious metal catalysts and low catalytic concentration, and is difficult to achieve industrial production. At present, the reaction substrate concentration is low; and the hydrogen pressure is high. It is difficult to achieve the industrial production of biobased adipic acid, which is still a technical problem that those skilled in the art have been trying to solve for a long time but cannot be solved. In view of this, the inventor has carried out a lot of research on the preparation technology of adipic acid.

The inventor has found from the research that the key point of industrial production of adipic acid is high yield at high substrate concentration, and the above double "high" can ensure low energy consumption of reaction and separation, which means low production cost: (1) a high substrate concentration means small reactor volume, less investment and high production intensity; (2) a high yield at high substrate concentration means a high concentration of a target product, and means low separation cost. At present, it has been reported that the low concentration of a muconic acid substrate (≤10 g/L) cannot be industrialized, and the reason for maintaining the low concentration of the substrate (muconic acid) is that the reactant itself is acidic and has catalytic performance, that is, under heating conditions, the muconic acid itself acts as a catalyst and a series of side reactions may occur through "autocatalysis". Therefore, the "bottleneck" technical difficulty of preparation of the biobased adipic acid is how to increase the substrate concentration and obtain a high yield of a target product.

In order to solve the above "bottleneck" technical difficulty, the present invention innovatively proposes an idea of using an efficient nickel-based hydrogenation catalyst to catalyze the hydrogenation of sodium muconate to prepare adipic acid, i.e., two key points of "efficient catalyst" and "sodium muconate": the muconic acid is alkalized to obtain the corresponding salt, which can eliminate the acidic property of the reactant itself, and solve the problem of self-catalysis caused by the reactant with carboxylic acid groups, thereby laying a foundation for increasing the substrate concentration. A special catalyst preparation method obtains an efficient catalyst (not only high activity, but also high selectivity), which ensures that only two C=C double bonds are hydrogenated in the reaction process, avoids side reactions such as C=C double bond hydration, and achieves a high yield of a target product.

Further, after extensive research, the inventor has found that the muconic acid hydrogenation reaction requires the catalyst to have good adsorption and desorption ability, and also to have excellent hydrogen activated dissociation ability. After screening, a neutral carrier is selected, which should have good ability of substrate adsorption and product desorption. After testing, alumina and SBA-15 have good carrier performance. For the selection of active metal, considering the economy, nickel is selected as the loaded active metal, and a nickel-based hydrogenation catalyst is innovatively constructed. Metal nickel is selected to replace precious metal as an active component, and metal nickel is loaded by a precipitation-deposition method. The preparation method of the nickel-based hydrogenation catalyst specifically comprises:

(1) Carrier pretreatment: a carrier is put into a $Na_2CO_3$ aqueous solution with a concentration of 0.1-0.8 M for ultrasonic pretreatment for 0-60 min, preferably 10-60 min; and after solid-liquid separation, the carrier is dried to obtain a pretreated carrier;

(2) The pretreated carrier is put into a flask and deionized water is added for ultrasonic treatment for 0-60 min, preferably 10-60 min, to obtain a carrier suspension with a concentration of 20-100 g/L and preferably 50-100 g/L;

(3) A nickel source is mixed with urea and deionized water to obtain a nickel source-urea mixed solution, the molar ratio of the urea to the nickel source is 2-8, and the mass ratio of the nickel source to water is 0.01-0.1;

(4) According to calculation based on the isoelectric point of the carrier, and according to the mass ratio 0.65-10 of the treated carrier to the nickel source, the carrier suspension is mixed with the nickel source-urea mixed solution; the mixture is sealed, stirred and impregnated at 30-100° C. for 2-6 h, preferably impregnated for 4-6 h, and more preferably 4 h; and then the flask is opened for stirring and drying at 30-100° C., preferably 90-100° C. and more preferably 90° C. until the water completely volatilizes to obtain a dry nickel-based catalyst precursor;

(5) The dry nickel-based catalyst precursor is put into a tube furnace in a hydrogen atmosphere for high-temperature reduction at 300-1000° C. for 60-300 min, and the obtained nickel-based hydrogenation catalyst should be stored in vacuum after the reduction.

In the above step (1), the mass ratio of the $Na_2CO_3$ aqueous solution to the carrier is 5-15:1.

In the present invention, the carrier comprises one or more of alumina powder, alumina pellets with a particle size between 20 and 100 meshes, SBA-15, silica gel, $SiO_2$, $TiO_2$ and activated carbon; and preferably, the alumina powder comprises one or more of α alumina, γ alumina and θ alumina.

In the present invention, the nickel source comprises many nickel sources such as nickel acetate and/or nickel nitrate.

In the above preparation method, the catalyst is reduced after impregnation. It should be noted that the optional operation of the drying step after the completion of the catalyst impregnation has many options such as drying in shade, baking and evaporation.

Figure 1:
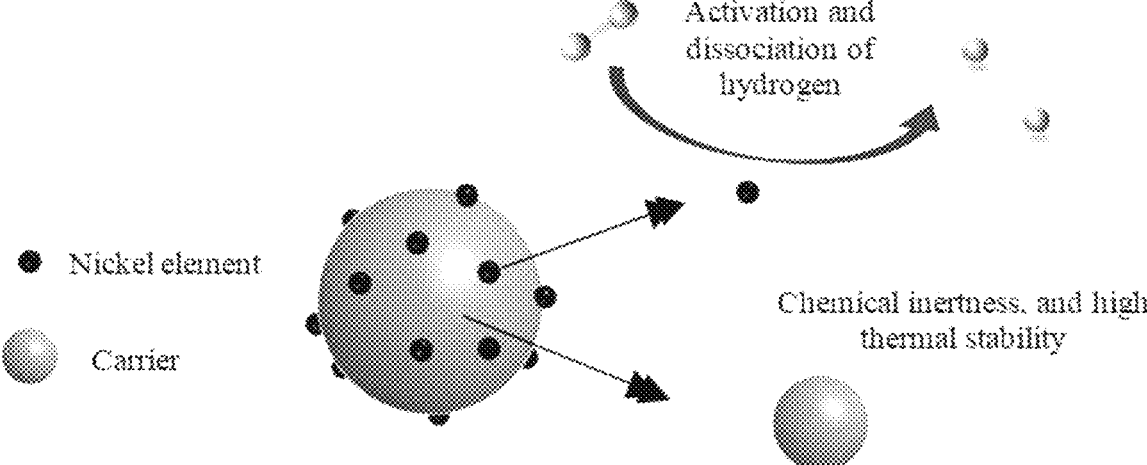
FIG. 1 shows a catalyst synthesis solution designed according to a reaction mechanism.

The nickel-based hydrogenation catalyst for preparing biobased adipic acid, prepared by the preparation method in the present invention is composed of carrier loaded metal nickel, and the action diagram of the nickel-based hydrogenation catalyst provided by the present invention is shown in FIG. 1.

The nickel-based hydrogenation catalyst prepared by the above method is correlatively characterized by BET characterization and TEM characterization. The detection results indicate that the average particle size of the metal nickel in the nickel-based hydrogenation catalyst is 2.5-4.5 nm, preferably 3.2-4.5 nm, and more preferably 3.2 nm. The specific surface area of the nickel-based hydrogenation catalyst is 50-300 m²/g, preferably 106.47-300 m²/g, and more preferably 106.47 m²/g. The load of the metal nickel in the nickel-based hydrogenation catalyst is between 2 wt % and 40 wt %, which proves that the metal nickel is highly dispersed on the surface of the catalyst carrier, thereby improving the catalytic performance and obtaining an economical and efficient nickel-based hydrogenation catalyst.

The research results indicate that nickel has a good interaction with hydrogen compared with other existing catalytically active metals of catalysts (such as precious metals Pt and Pd), has the cost of ⅓₀₀₀ of Pt and ¹⁄₁₈₀₀ of Pd, and has more industrial value.

Figure 4:
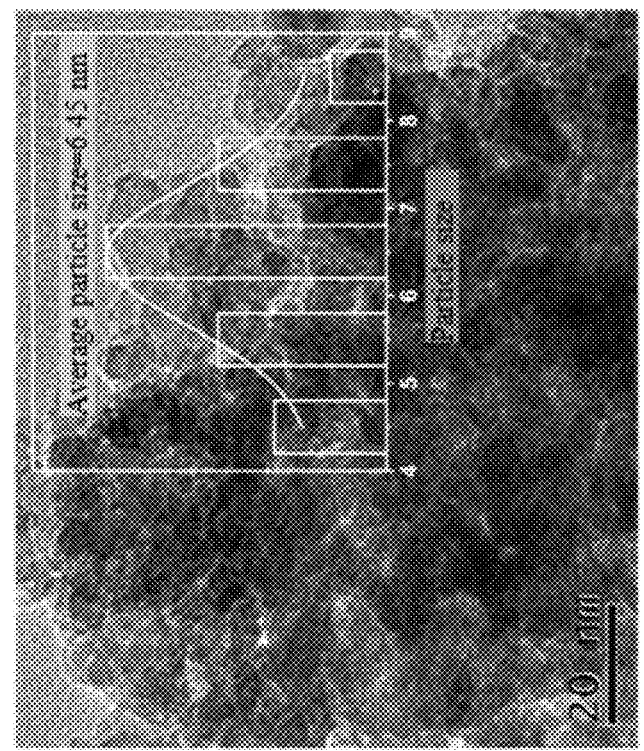
FIG. 4 shows a comparison diagram of TEM characterization particle size between a nickel-based catalyst prepared in embodiment 1 and a nickel-based catalyst prepared by the traditional impregnation method (the two catalysts are only prepared in different methods, and the rest are consistent), wherein the left figure is a statistical diagram of the particle size of the nickel-based catalyst prepared by the present invention, and the right figure is a statistical diagram of the particle size of the catalyst prepared by the traditional impregnation method.
Figure 4:
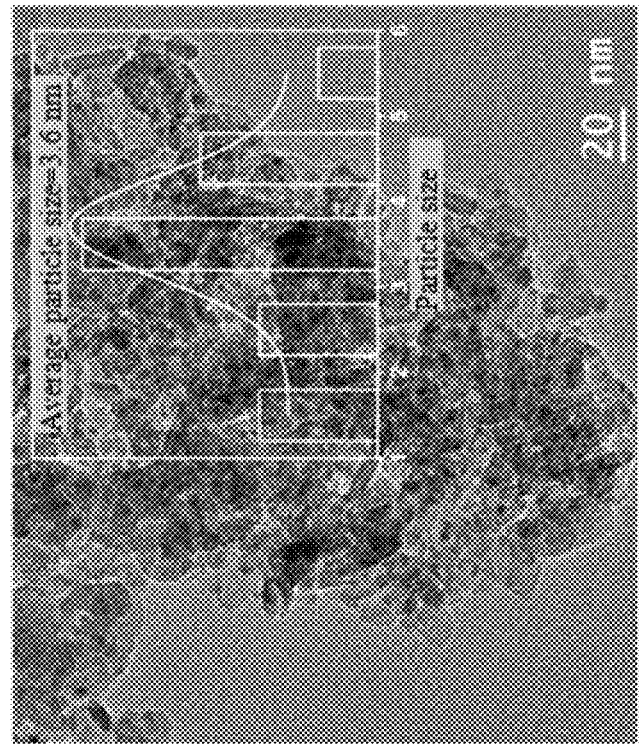

The nickel-based catalyst provided by the present invention is compared with the catalyst prepared by the traditional impregnation method, and the relevant TEM characterization diagrams are shown in FIG. 4. In FIG. 4, the left figure shows the nickel-based catalyst prepared by the improved method of the present invention, and the right figure shows the catalyst prepared by the traditional impregnation method. It can be obviously observed that the catalyst prepared by the method of the present invention has uniform distribution of the loaded metal, has an average particle size only about half that of the traditional method, and shows higher dispersion, which also explains the superior hydrogenation performance.

Figure 2:
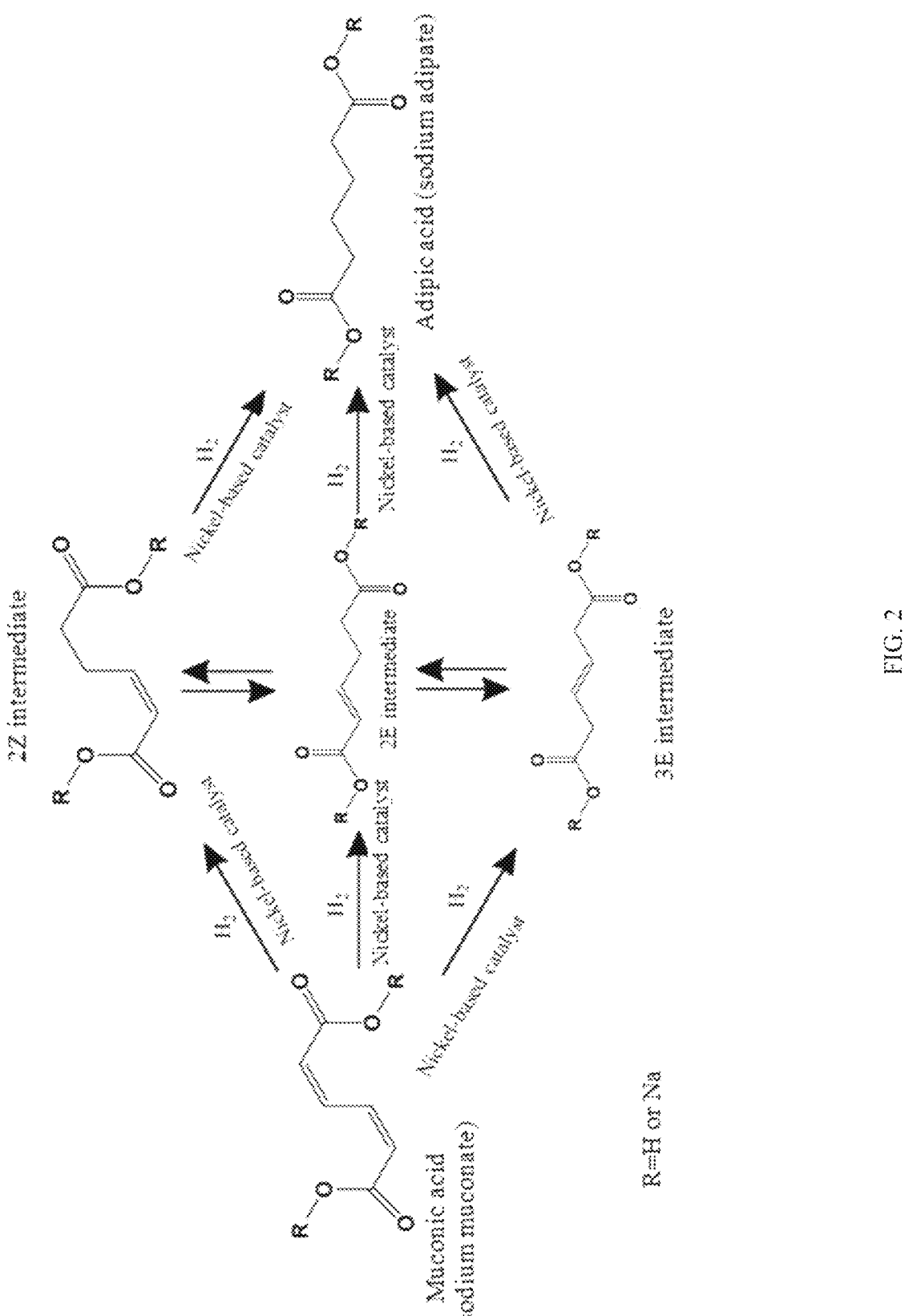
FIG. 2 shows a reaction process of preparing adipic acid (sodium) based on catalytic hydrogenation of muconic acid (sodium muconate), wherein R=H or Na.

In the present invention, it should be understood that because cis-muconic acid is extremely difficult to dissolve at room temperature, it can be considered insoluble at room temperature. The solubility is increased with the increase of temperature, but is extremely limited. When the temperature is increased to 70° C., the solubility of muconic acid in water is only about 70 g/L, so muconic acid can be directly used as a reactant in some low-concentration experiments. However, at higher concentrations, sodium muconate can only be used as a substrate in the reaction. Moreover, in the fermentation of biobased muconic acid, due to the need of pH regulation (usually using sodium hydroxide), the obtained product is usually cis-sodium muconate, so the use of sodium muconate as a substrate is conducive to better docking of upstream technologies. Biobased muconic acid refers to biobased muconic acid obtained by separation, purification and other steps of fermentation broth obtained from microbial fermentation. The hydrogenation reaction path of cis-muconic acid is shown in FIG. 2.

In order to realize the production of biobased adipic acid, the present invention also provides a hydrogenation reaction system for preparing biobased adipic acid, and the main reaction device is a batch stirring reactor or a microreaction device.

In the present invention, the microreaction device for the preparation of adipic acid by catalytic hydrogenation of biobased sodium muconate using the above nickel-based hydrogenation catalyst is shown in FIG. 3. It can be seen from FIG. 3 that the microreaction device comprises a reaction liquid storage tank, a constant-flux pump, a micromixer, a micro packed bed reactor, a phase separator and a product collector connected successively; a hydrogen source is connected with the micromixer; a gas flow meter is arranged between the hydrogen source and the micromixer; and a back pressure valve is arranged on the phase separator.

In the present invention, the micro packed bed reactor can adopt a steel pipe with an inner diameter of 0.5-10 mm, preferably 0.5-3 mm, and a length of 2-20 cm, preferably 3-12 cm.

The present invention further provides a preparation method of biobased adipic acid with industrial prospect, which comprises conducting a hydrogenation reaction on biobased muconic acid or biobased sodium muconate for preparing adipic acid in the hydrogenation reaction system under the action of the nickel-based hydrogenation catalyst of the present invention.

According to some embodiments of the present invention, when the main reaction device of the hydrogenation reaction system is the batch stirring reactor, the preparation method of the biobased adipic acid comprises putting the nickel-based hydrogenation catalyst into the batch stirring reactor, adding a biobased muconic acid aqueous solution or a sodium muconate aqueous solution, and filling the reactor with hydrogen for a hydrogenation catalytic reaction on a matched heating sleeve to obtain adipic acid.

The reaction conditions for preparing adipic acid by the batch stirring reactor are as follows:

(1) The concentration of the biobased muconic acid aqueous solution or the sodium muconate aqueous solution is ≥10 g/L, preferably 50-200 g/L;

(2) A mass ratio of the biobased muconic acid or sodium muconate to the nickel-based hydrogenation catalyst is 1-50, preferably 20-40;

(3) The pressure of hydrogen in the batch stirring reactor is 0.1-5 MPa, preferably 0.8-1.5 MPa;

(4) The temperature of the hydrogenation reaction is 50-200° C., preferably 70-90° C.; and the time of hydrogenation reaction is 5 min-24 h, preferably 30 min-6 h.

Figure 5:
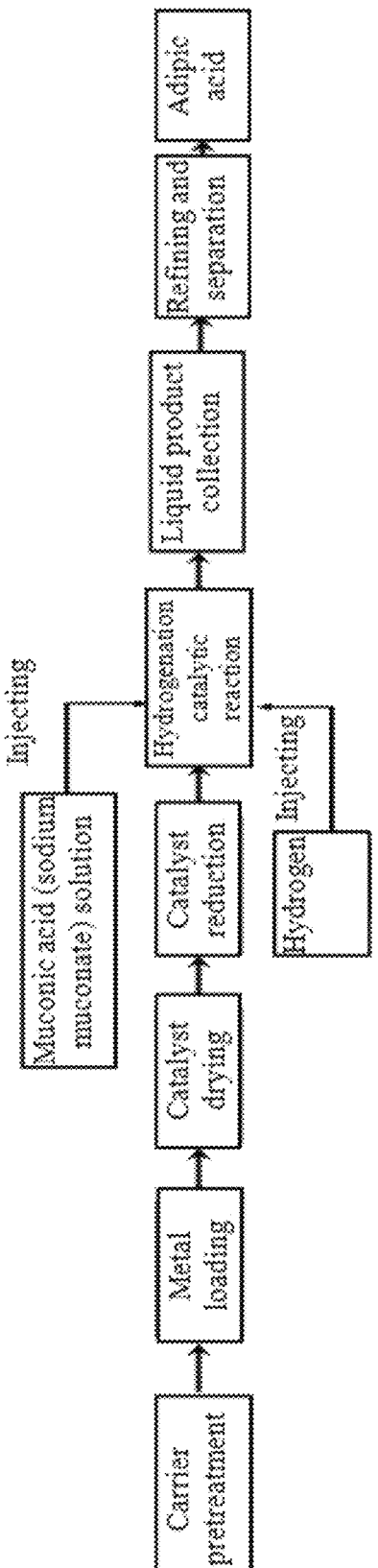
FIG. 5 is a schematic diagram of a process flow for producing biobased adipic acid in the present invention.

According to other embodiments of the present invention, when the main reaction device of the hydrogenation reaction system is the microreaction device, a flow chart of a reaction technology of preparing adipic acid by using the microreaction device is shown in FIG. 5. The preparation method of the biobased adipic acid comprises: filling the steel pipe used as a micro packed bed reactor with the nickel-based hydrogenation catalyst; filling both ends of the steel pipe with inert material (such as inert glass beads) to prevent the catalyst from leaking out; injecting the muconic acid aqueous solution or the sodium muconate aqueous solution and hydrogen into the micro packed bed reactor; heating the micro packed bed reactor in a water bath or an oil bath to conduct a catalytic hydrogenation reaction; collecting a liquid product; and refining (such as cooling or acidification and cooling) and separating the liquid product to obtain an adipic acid product.

According to the present invention, when the microreaction device is used for reaction, the nickel-based hydrogenation catalyst is filled into the micro packed bed reactor, including: a powdered nickel-based hydrogenation catalyst prepared by a powder carrier is firstly pressed, formed and sieved, and then filled into the micro packed bed reactor, or a spherical hydrogenation catalyst prepared by a spherical carrier is directly filled into the micro packed bed reactor. The height of the filled catalyst bed is 2-15 cm, preferably 3-10 cm; and both ends of the filled catalyst bed are filled with the inert glass beads.

The reaction conditions for preparing adipic acid by using the microreaction device are as follows:

(1) The molar concentration of the biobased muconic acid aqueous solution or the sodium muconate aqueous solution is ≥10 g/L, preferably 50-200 g/L;

(2) The flow rate of the injected biobased muconic acid aqueous solution or the sodium muconate aqueous solution is controlled by the constant-flux pump, and the flow rate is preferably 0.1-2 mL/min;

(3) The pressure of hydrogen injected into the micro packed bed reactor is 0.16-10.0 MPa, preferably 0.5-5.0 MPa;

(4) The flow rate of the injected hydrogen is controlled by a gas flow meter, and preferably the flow rate of the injected hydrogen is 10-100 mL/min;

(5) The temperature of the hydrogenation reaction is 30-200° C., preferably 30-120° C.; and the time of the hydrogenation reaction is 10 s-10 min, preferably 20 s-4 min.

In the present invention, the biobased muconic acid is prepared by fermentation.

The present invention applies the micro packed bed technology to the catalytic hydrogenation reaction of muconic acid for the first time, realizes the complete conversion of 200 g/L biobased sodium muconate into adipic acid when the reaction time is 18 h in the reactor, and realizes a yield 100 mol % of the target product sodium adipate at the residence time of about 3 min when the concentration of substrate material liquid (biobased sodium muconate solution) is up to 200 g/L in the microreactor. The spatio-temporal yield is increased compared with that of the reactor by nearly 20 times, and the reaction solvent of both reactors is water, which greatly improves the degree of greening of the reaction process.

III. Embodiments

The present invention is explained below in detail through specific embodiments. The experimental methods described below are conventional laboratory methods unless otherwise specified. The experimental materials described below are commercially available unless otherwise specified.

The following embodiments include catalyst preparation and hydrogenation reaction technologies. In the following embodiments, nickel-based catalysts synthesized under different conditions are characterized by TEM, and the average particle size is between 2.5-4.5 nm. After BET characterization, the synthesized nickel-based catalysts are well dispersed with specific surface area between 50-300 $m^2$/g:

In the following embodiments, the reaction liquid component, i.e., a liquid product is determined by high performance liquid chromatography. The liquid product is analyzed by using Rezex-ROA organic acid H+column (300×

7.8 mm, Phenomenex) at 393 K and a mobile phase flow rate equal to 0.06 mL/min. A 5 mmol sulfuric acid solution is selected as a mobile phase to eluate the sample. The whole analysis lasts 40 minutes. The concentration of organic acid is quantified by a refractive index detector (RID) by using an external standard calibration method, and the raw material conversion rate, catalyst selectivity and adipic acid yield are calculated by the following formulas (I) to (III).

$$\text{Converstion Rate } X \, (\%) = 100\% \times \left[ (n_0 - n_1)/n_0 \right] \qquad \text{Formula (I)}$$

In formula (I):

$n_0$ is the mass of the initial substance of the added biobased sodium muconate, in g;

$n_1$ is the remaining mass of the biobased sodium muconate after the reaction is completed, in g.

$$\text{Converstion rate } S \, (\%) = 100\% \times \left[ n_{AdA}/(n_0 - n_1) \right] \qquad \text{Formula (II)}$$

In formula (II):

$n_0$ is the initial mass of the added biobased sodium muconate, in g;

$n_1$ is the remaining mass of the biobased sodium muconate after the reaction is completed, in g;

$n_{AdA}$ is the mass of product sodium adipate after the reaction is completed, in g.

$$\text{Conversion rate } Y \, (\%) = 100\% \times \left( n_{AdA}/n_0 \right) \qquad \text{Formula (III)}$$

In formula (III):

$n_0$ is the initial mass of the added biobased sodium muconate, in g;

$n_{AdA}$ is the mass of product sodium adipate after the reaction is completed, in g.

Embodiment 1

(1) Carrier pretreatment: a carrier is put into a $Na_2CO_3$ aqueous solution with a concentration of 0.5 M for ultrasonic treatment for 30 min; and after solid-liquid separation, the carrier is dried to obtain pretreated carrier powder;

(2) 10 g of alumina powder (pretreated carrier powder) and 200 mL of water are added into a 250 mL flask for ultrasonic shaking for 30 min to obtain a carrier suspension with a concentration of 50 g/L;

(3) Nickel nitrate and an appropriate amount of urea are dissolved in 50 mL of deionized water (a mass ratio of a nickel source to water is 0.05), and the molar ratio of urea to the nickel source is 4 to obtain a nickel source-urea mixed solution.

(4) The carrier suspension is mixed with the nickel source-urea mixed solution; the mixture is added to a jacketed beaker, sealed and stirred in a water bath at 90° C. for 4 h; and then the catalyst is dried in a water bath at 90° C. to obtain a dry nickel-based hydrogenation catalyst precursor;

(5) The dry nickel-based hydrogenation catalyst precursor is placed in a tube furnace; hydrogen is injected for reducing at high temperature of 300° C. for 4 hours;

and after the reduction is ended, the obtained nickel-based hydrogenation catalyst should be stored in vacuum.

(6) The prepared nickel-based hydrogenation catalyst is pressed, sieved and filled in a steel pipe with diameter of ¼ inch (inner diameter of 0.635 cm). Both ends of the steel pipe are filled with inert glass microbeads to prevent the catalyst from leaking. The hydrogen and the prepared biobased sodium muconate solution (200 g/L) are injected into the reactor. The flow rate of the liquid is controlled by a constant-flux pump, and the flow rate of the injected biobased sodium muconate solution is 0.1 mL/min. The gas flow rate is controlled by a gas flowmeter, the flow rate is 10 mL/min, and the pressure of hydrogen in the reactor is 3 MPa. The microreactor requires a water/oil bath to maintain the reaction temperature. The reaction is conducted at 80° C. The inner diameter of the reactor is ¼ inch, the height of the catalyst bed is 10 cm, (residence time of 157 s), and the reaction is conducted for 157 s.

(7) The liquid product is analyzed by using Rezex-ROA organic acid H+column (300×7.8 mm, Phenomenex) at 393 K and a mobile phase flow rate equal to 0.06 mL/min. A 5 mmol sulfuric acid solution is selected as a mobile phase to eluate the sample. The whole analysis lasts 40 minutes. The concentration of organic acid is quantified by a refractive index detector (RID) by using an external standard calibration method.

According to formulas (I), (II) and (III), testing and calculation are conducted. The conversion rate of the biobased sodium muconate is 100%, the selectivity of adipic acid is 99.2%, and the yield of adipic acid is 99.2%.

Embodiment 2

The present embodiment is different from embodiment 1 in that:

The reaction is conducted in a kettle reactor under the conditions of hydrogen pressure of 1 MPa, substrate concentration of 10 g/L, reaction time of 6 h, magnetic stirring at 600 RPM, and at 60° C.

Other reaction conditions are the same as those of embodiment 1.

According to formulas (I), (II) and (III), testing and calculation are conducted. The conversion rate of the biobased sodium muconate is 70.6%, the selectivity of adipic acid is 86.5%, and the yield of adipic acid is 61.1%.

Embodiment 3

The present embodiment is different from embodiment 1 in that:

The reaction is conducted in a kettle reactor under the conditions of hydrogen pressure of 1 MPa, substrate concentration of 10 g/L, reaction time of 6 h, magnetic stirring at 600 RPM, and at 70° C.

Other reaction conditions are the same as those of embodiment 1.

According to formulas (I), (II) and (III), testing and calculation are conducted. The conversion rate of the biobased sodium muconate is 89.9%, the selectivity of adipic acid is 82.3%, and the yield of adipic acid is 74.0%.

Embodiment 4

The present embodiment is different from embodiment 1 in that:

The reaction is conducted in a kettle reactor under the conditions of hydrogen pressure of 1 MPa, substrate concentration of 10 g/L, reaction time of 6 h, magnetic stirring at 600 RPM, and at 80° C.

Other reaction conditions are the same as those of embodiment 1.

According to formulas (I), (II) and (III), testing and calculation are conducted. The conversion rate of the biobased sodium muconate is 100%, the selectivity of adipic acid is 96.3%, and the yield of adipic acid is 96.3%.

Embodiment 5

The present embodiment is different from embodiment 1 in that:

The reaction is conducted in a kettle reactor under the conditions of hydrogen pressure of 1 MPa, substrate concentration of 10 g/L, reaction time of 6 h, magnetic stirring at 600 RPM, and at 90° C.

Other reaction conditions are the same as those of embodiment 1.

According to formulas (I), (II) and (III), testing and calculation are conducted. The conversion rate of the biobased sodium muconate is 100%, the selectivity of adipic acid is 99.0%, and the yield of adipic acid is 99.0%.

Embodiment 6

The present embodiment is different from embodiment 1 in that:

The reaction is conducted in a kettle reactor under the conditions of hydrogen pressure of 1 MPa, substrate concentration of 10 g/L, reaction time of 6 h, magnetic stirring at 600 RPM, and at 100° C.

Other reaction conditions are the same as those of embodiment 1.

According to formulas (I), (II) and (III), testing and calculation are conducted. The conversion rate of the biobased sodium muconate is 100%, the selectivity of adipic acid is 99.6%, and the yield of adipic acid is 99.6%.

The reaction conditions of embodiments 2-6 are compared with those of embodiment 1, and the results are shown in Table 1 below.

TABLE 1

| | | Conversion | | |
|---|---|---|---|---|
| | Different Conditions | rate | Selectivity | Yield |
| Comparison of Conditions of Embodiments 2-6 and Embodiment 1 | | | | |
| Embodiment 1 | Reaction is conducted in the microreactor at 80° C. The substrate concentration is 200 g/L Reaction is conducted for 157 s The hydrogen pressure is 3 MPa | 100% | 99.2% | 99.2% |

TABLE 1-continued

Comparison of Conditions of Embodiments 2-6 and Embodiment 1

|  | Different Conditions | Conversion rate | Selectivity | Yield |
|---|---|---|---|---|
| Embodiment 2 | Reaction is conducted in the reactor at 60° C. The substrate concentration is 10 g/L Reaction is conducted for 6 h The hydrogen pressure is 1 MPa | 70.6% | 86.5% | 61.1% |
| Embodiment 3 | Reaction is conducted in the reactor at 70° C. The substrate concentration is 10 g/L Reaction is conducted for 6 h The hydrogen pressure is 1 MPa | 89.9% | 82.3% | 74.0% |
| Embodiment 4 | Reaction is conducted in the reactor at 80° C. The substrate concentration is 10 g/L Reaction is conducted for 6 h The hydrogen pressure is 1 MPa | 100% | 96.3% | 96.3% |
| Embodiment 5 | Reaction is conducted in the reactor at 90° C. The substrate concentration is 10 g/L Reaction is conducted for 6 h The hydrogen pressure is 1 MPa | 100% | 99.0% | 99.0% |
| Embodiment 6 | Reaction is conducted in the reactor at 100° C. The substrate concentration is 10 g/L Reaction is conducted for 6 h The hydrogen pressure is 1 MPa | 100% | 99.6% | 99.6% |

Embodiment 7

The present embodiment is different from embodiment 1 in that:

The reaction is conducted in a kettle reactor under the conditions of reaction time of 18 h, magnetic stirring at 600 RPM, and at 80° C.

Other reaction conditions are the same as those of embodiment 1.

According to formulas (I), (II) and (III), testing and calculation are conducted. The conversion rate of the biobased sodium muconate is 100%, the selectivity of adipic acid is 99.8%, and the yield of adipic acid is 99.8%.

Embodiment 8

The present embodiment is different from embodiment 1 in that:

The reaction is conducted in a kettle reactor under the conditions of reaction time of 12 h, magnetic stirring at 600 RPM, and at 80° C.

Other reaction conditions are the same as those of embodiment 1.

According to formulas (I), (II) and (III), testing and calculation are conducted. The conversion rate of the biobased sodium muconate is 100%, the selectivity of adipic acid is 89.8%, and the yield of adipic acid is 89.8%.

Embodiment 9

The present embodiment is different from embodiment 1 in that:

The reaction is conducted in a kettle reactor under the conditions of reaction time of 6 h, magnetic stirring at 600 RPM, and at 80° C.

Other reaction conditions are the same as those of embodiment 1.

According to formulas (I), (II) and (III), testing and calculation are conducted. The conversion rate of the biobased sodium muconate is 64.8%, the selectivity of adipic acid is 74.2%, and the yield of adipic acid is 48.1%.

Embodiment 10

The present embodiment is different from embodiment 1 in that:

The reaction is conducted in a kettle reactor under the conditions of reaction time of 3 h, magnetic stirring at 600 RPM, and at 80° C.

Other reaction conditions are the same as those of embodiment 1.

According to formulas (I), (II) and (III), testing and calculation are conducted. The conversion rate of the biobased sodium muconate is 32.6%, the selectivity of adipic acid is 47.5%, and the yield of adipic acid is 15.5%.

The reaction conditions of embodiments 7-10 are compared with those of embodiment 1, and the results are shown in Table 2 below.

TABLE 2

Comparison of Conditions of Embodiments 7-10 and Embodiment 1 (Substrate Concentrations of 200 g/L)

|  | Different Conditions | Conversion Rate | Selectivity | Yield |
|---|---|---|---|---|
| Embodiment 1 | Reaction for 157 s in microreactor | 100% | 99.2% | 99.2% |

TABLE 2-continued

| | Different Conditions | Conversion Rate | Selectivity | Yield |
|---|---|---|---|---|
| Comparison of Conditions of Embodiments 7-10 and Embodiment 1 (Substrate Concentrations of 200 g/L) | | | | |
| Embodiment 7 | Reaction for 18 h in the reactor | 100% | 99.8% | 99.8% |
| Embodiment 8 | Reaction for 12 h in the reactor | 100% | 89.8% | 89.8% |
| Embodiment 9 | Reaction for 6 h in the reactor | 64.8% | 74.2% | 48.1% |
| Embodiment 10 | Reaction for 3 h in the reactor | 32.6% | 47.5% | 15.5% |

Embodiment 11

The present embodiment is different from embodiment 1 in that:

5 g of SBA-15 zeolite is added in step (2). In step (3), the substrate concentration is 10 g/L and the hydrogen pressure is 1 MPa.

Other reaction conditions are the same as those of embodiment 1.

According to formulas (I), (II) and (III), testing and calculation are conducted. The conversion rate of the biobased sodium muconate is 100%, the selectivity of adipic acid is 98.6%, and the yield of adipic acid is 98.6%.

Embodiment 12

The present embodiment is different from embodiment 1 in that:

5 g of alumina pellets are added in step (2). In step (3), the substrate concentration is 10 g/L and the hydrogen pressure is 1 MPa.

Other reaction conditions are the same as those of embodiment 1.

According to formulas (I), (II) and (III), testing and calculation are conducted. The conversion rate of the biobased sodium muconate is 100%, the selectivity of adipic acid is 98.4%, and the yield of adipic acid is 98.4%.

The reaction conditions of embodiments 11-12 are compared with those of embodiment 1, and the results are shown in Table 3 below.

TABLE 3

| | Different Conditions | Conversion rate | Selectivity | Yield |
|---|---|---|---|---|
| Comparison of Conditions of Embodiments 11-12 and Embodiment 1 | | | | |
| Embodiment 1 | The carrier is γ-alumina The substrate concentration is 200 g/L The hydrogen pressure is 3 MPa | 100% | 99.2% | 99.2% |
| Embodiment 11 | The carrier is SBA-15 The substrate concentration is 10 g/L The hydrogen pressure is 1 MPa | 100% | 98.6% | 98.6% |
| Embodiment 12 | The carrier is alumina pellet The substrate concentration is 10 g/L The hydrogen pressure is 1 MPa | 100% | 98.4% | 98.4% |

Embodiment 13

The present embodiment is different from embodiment 1 in that:

5 g of alumina pellets are added in step (2). The reaction temperature is 70° C. In step (4), the substrate concentration is 10 g/L, and the hydrogen pressure is 1 MPa.

Other reaction conditions are the same as those of embodiment 1.

According to formulas (I), (II) and (III), testing and calculation are conducted. The conversion rate of the biobased sodium muconate is 90.2%, the selectivity of adipic acid is 84.6%, and the yield of adipic acid is 76.3%.

Embodiment 14

The present embodiment is different from embodiment 1 in that:

5 g of alumina pellets are added in step (2). The reaction temperature is 80° C. In step (4), the substrate concentration is 10 g/L, and the hydrogen pressure is 1 MPa.

Other reaction conditions are the same as those of embodiment 1.

According to formulas (I), (II) and (III), testing and calculation are conducted. The conversion rate of the biobased sodium muconate is 100%, the selectivity of adipic acid is 94.6%, and the yield of adipic acid is 94.6%.

Embodiment 15

The present embodiment is different from embodiment 1 in that:

5 g of alumina pellets are added in step (2). The reaction temperature is 90° C. In step (4), the substrate concentration is 10 g/L, and the hydrogen pressure is 1 MPa.

Other reaction conditions are the same as those of embodiment 1.

According to formulas (I), (II) and (III), testing and calculation are conducted. The conversion rate of the biobased sodium muconate is 100%, the selectivity of adipic acid is 98.6%, and the yield of adipic acid is 98.6%.

Embodiment 16

The present embodiment is different from embodiment 1 in that:

5 g of alumina pellets are added in step (2). The reaction temperature is 100° C. In step (4), the substrate concentration is 10 g/L, and the hydrogen pressure is 1 MPa.

Other reaction conditions are the same as those of embodiment 1.

According to formulas (I), (II) and (III), testing and calculation are conducted. The conversion rate of the biobased sodium muconate is 100%, the selectivity of adipic acid is 99.4%, and the yield of adipic acid is 99.4%.

The reaction conditions of embodiments 13-16 are compared with those of embodiment 1, and the results are shown in Table 4 below.

According to formulas (I), (II) and (III), testing and calculation are conducted. The conversion rate of the biobased sodium muconate is 100%, the selectivity of adipic acid is 99.4%, and the yield of adipic acid is 99.4%.

Embodiment 19

The present embodiment is different from embodiment 1 in that:

In step (4), 2 MPa of hydrogen is added and the reaction temperature is 80° C. The substrate concentration is 10 g/L.

Other reaction conditions are the same as those of embodiment 1.

According to formulas (I), (II) and (III), testing and calculation are conducted. The conversion rate of the

TABLE 4

Comparison of Conditions of Embodiments 13-16 and Embodiment 1

| | Different Conditions | Conversion rate | Selectivity | Yield |
|---|---|---|---|---|
| Embodiment 1 | The reaction temperature is 80° C. The substrate concentration is 200 g/L The hydrogen pressure is 3 MPa | 100% | 99.2% | 99.2% |
| Embodiment 13 | The reaction temperature is 60° C. The substrate concentration is 10 g/L The hydrogen pressure is 1 MPa | 90.2% | 84.6% | 76.3% |
| Embodiment 14 | The reaction temperature is 70° C. The substrate concentration is 10 g/L The hydrogen pressure is 1 MPa | 100% | 94.6% | 94.6% |
| Embodiment 15 | The reaction temperature is 80° C. The substrate concentration is 10 g/L The hydrogen pressure is 1 MPa | 100% | 98.6% | 98.6% |
| Embodiment 16 | The reaction temperature is 90° C. The substrate concentration is 10 g/L The hydrogen pressure is 1 MPa | 100% | 99.4% | 99.4% |

Embodiment 17

The present embodiment is different from embodiment 1 in that:

In step (4), 0.5 MPa of hydrogen is added and the reaction temperature is 80° C. The substrate concentration is 10 g/L.

Other reaction conditions are the same as those of embodiment 1.

According to formulas (I), (II) and (III), testing and calculation are conducted. The conversion rate of the biobased sodium muconate is 100%, the selectivity of adipic acid is 74.2%, and the yield of adipic acid is 74.2%.

Embodiment 18

The present embodiment is different from embodiment 1 in that:

In step (4), 1.5 MPa of hydrogen is added and the reaction temperature is 80° C. The substrate concentration is 10 g/L.

Other reaction conditions are the same as those of embodiment 1.

biobased sodium muconate is 100%, the selectivity of adipic acid is 99.5%, and the yield of adipic acid is 99.5%.

Embodiment 20

The present embodiment is different from embodiment 1 in that:

In step (4), 3 MPa of hydrogen is added and the reaction temperature is 80° C. The substrate concentration is 10 g/L.

Other reaction conditions are the same as those of embodiment 1.

According to formulas (I), (II) and (III), testing and calculation are conducted. The conversion rate of the biobased sodium muconate is 100%, the selectivity of adipic acid is 100%, and the yield of adipic acid is 100%.

The reaction conditions of embodiments 17-20 are compared with those of embodiment 1, and the results are shown in Table 5 below.

TABLE 5

Comparison of Conditions of Embodiments 17-20 and Embodiment 1

| | Different Conditions | Conversion rate | Selectivity | Yield |
|---|---|---|---|---|
| Embodiment 1 | The reaction temperature is 80° C. 3 MPa of hydrogen is added, and the substrate concentration is 200 g/L | 100% | 99.2% | 99.2% |
| Embodiment 17 | The reaction temperature is 80° C. 0.5 MPa of hydrogen is added, and the substrate concentration is 10 g/L | 100% | 74.2% | 74.2% |
| Embodiment 18 | The reaction temperature is 80° C. 1.5 MPa of hydrogen is added, and the substrate concentration is 10 g/L | 100% | 99.4% | 99.4% |
| Embodiment 19 | The reaction temperature is 80° C. 2 MPa of hydrogen is added, and the substrate concentration is 10 g/L | 100% | 99.5% | 99.5% |
| Embodiment 20 | The reaction temperature is 80° C. 3 MPa of hydrogen is added, and the substrate concentration is 10 g/L | 100% | 100% | 100% |

Embodiment 21

The present embodiment is different from embodiment 1 in that:

In step (4), 30 g/L biobased sodium muconate solution is added to react for 1 min. The reaction temperature is 80° C. 1 MPa of hydrogen is added.

Other reaction conditions are the same as those of embodiment 1.

According to formulas (I), (II) and (III), testing and calculation are conducted. The conversion rate of the biobased sodium muconate is 100%, the selectivity of adipic acid is 98.6%, and the yield of adipic acid is 98.6%.

Embodiment 22

The present embodiment is different from embodiment 1 in that:

In step (4), 50 g/L biobased sodium muconate solution is added to react for 1 min. The reaction temperature is 80° C. 1 MPa of hydrogen is added.

Other reaction conditions are the same as those of embodiment 1.

According to formulas (I), (II) and (III), testing and calculation are conducted. The conversion rate of the biobased sodium muconate is 100%, the selectivity of adipic acid is 98.4%, and the yield of adipic acid is 98.4%.

Embodiment 23

The present embodiment is different from embodiment 1 in that:

In step (4), 70 g/L biobased sodium muconate solution is added to react for 1 min. The reaction temperature is 80° C. 1 MPa of hydrogen is added.

Other reaction conditions are the same as those of embodiment 1.

According to formulas (I), (II) and (III), testing and calculation are conducted. The conversion rate of the biobased sodium muconate is 100%, the selectivity of adipic acid is 99.4%, and the yield of adipic acid is 99.4%.

Embodiment 24

The present embodiment is different from embodiment 1 in that:

In step (4), 100 g/L biobased sodium muconate solution is added to react for 80 s. The reaction temperature is 80° C. 1.5 MPa of hydrogen is added. The hydrogen pressure is 1.5 MPa.

Other reaction conditions are the same as those of embodiment 1.

According to formulas (I), (II) and (III), testing and calculation are conducted. The conversion rate of the biobased sodium muconate is 100%, the selectivity of adipic acid is 99.6%, and the yield of adipic acid is 99.6%.

The reaction conditions of embodiments 21-24 are compared with those of embodiment 1, and the results are shown in Table 6 below.

TABLE 6

Comparison of Conditions of Embodiments 21-24 and Embodiment 1

| | Different Conditions | Conversion rate | Selectivity | Yield |
|---|---|---|---|---|
| Embodiment 1 | The reaction temperature is 80° C. 3 MPa of hydrogen is added Reaction is conducted for 157 s The substrate concentration is 200 g/L | 100% | 99.2% | 99.2% |

TABLE 6-continued

| | | Conversion rate | Selectivity | Yield |
|---|---|---|---|---|
| | Comparison of Conditions of Embodiments 21-24 and Embodiment 1 | | | |
| | Different Conditions | | | |
| Embodiment 21 | The reaction temperature is 80° C. Reaction is conducted for 60 s The substrate concentration is 30 g/L | 100% | 98.6% | 98.6% |
| Embodiment 22 | The reaction temperature is 80° C. Reaction is conducted for 60 s The substrate concentration is 50 g/L | 100% | 98.4% | 98.4% |
| Embodiment 23 | The reaction temperature is 80° C. Reaction is conducted for 60 s The substrate concentration is 70 g/L | 100% | 99.4% | 99.4% |
| Embodiment 24 | The reaction temperature is 80° C. 1.5 MPa of hydrogen is added Reaction is conducted for 80 s The substrate concentration is 100 g/L | 100% | 99.6% | 99.6% |

Embodiment 25

The present embodiment is different from embodiment 1 in that:

The nickel-based catalyst is prepared by the traditional impregnation method.

Other reaction conditions are the same as those of embodiment 1.

According to formulas (I), (II) and (III), testing and calculation are conducted. The conversion rate of the biobased sodium muconate is 54.1%, the selectivity of adipic acid is 42.6%, and the yield of adipic acid is 23.1%.

The reaction conditions of embodiment 25 are compared with those of embodiment 1, and the results are shown in Table 7 below.

TABLE 7

| | | Conversion rate | Selectivity | Yield |
|---|---|---|---|---|
| | Comparison of Conditions of Embodiment 25 and Embodiment 1 | | | |
| | Different Conditions | | | |
| Embodiment 1 | The catalyst is prepared by the improved method of the present invention | 100% | 99.2% | 99.2% |
| Embodiment 25 | The catalyst is prepared by the traditional impregnation method | 54.1% | 42.6% | 23.1% |

It should be noted that the above embodiments are only used to explain the present invention, and do not constitute any limitation to the present invention. The present invention is described by reference to typical embodiments, but it should be understood that the words used therein are descriptive and explanatory words, and not restrictive words. The present invention may be modified within the scope of the claims of the present invention as specified, and may be revised without departing from the scope and the spirit of the present invention. Although the present invention described herein relates to specific methods, materials and embodiments, it is not meant that the present invention is limited to specific embodiments disclosed therein, but rather that the present invention may be extended to all other methods and applications with the same functions.

What is claimed is:

1. A preparation method of biobased adipic acid, comprising preparing a nickel-based hydrogenation catalyst, and conducting a hydrogenation reaction on biobased sodium muconate for preparing adipic acid in a microreactor under the action of the nickel-based hydrogenation catalyst; wherein the preparing the nickel-based hydrogenation catalyst comprises carrier pretreatment and metal nickel loading by a precipitation-deposition method, comprising:

step A: putting a carrier into an aqueous solution consisting of 0.5 M $Na_2CO_3$ and water, performing ultrasonic pretreatment for 30 min; and after solid-liquid separation, drying the carrier to obtain a pretreated carrier, wherein the carrier is alumina powder;

step B: adding 10 g of the pretreated carrier to 200 ml of water for ultrasonic shaking for 30 min to obtain a carrier suspension with a concentration of 50 g/L;

step C: mixing a nickel source with urea and 50 mL of deionized water to obtain a nickel source-urea mixed solution, wherein a mass ratio of the nickel source to deionized water is 0.05, and a molar ratio of urea to the nickel source is 4;

step D: mixing the carrier suspension with the nickel source-urea mixed solution; adding to a jacketed beaker, and sealing and stirring in a water bath at 90° C. for 4 h for impregnating; then unsealing, stirring and drying in a water bath at 90° C. until the water completely volatilizes to obtain a dry nickel-based hydrogenation catalyst precursor;

step E: placing the dry nickel-based hydrogenation catalyst precursor in a tube furnace; injecting hydrogen for reducing at high temperature of 300° C. for 4 hours to obtain a nickel-based hydrogenation catalyst;

step F: pressing, sieving and filling the nickel-based hydrogenation catalyst in a steel pipe with an inner diameter of 0.635 cm, where both ends of the steel pipe are filled with inert glass microbeads to prevent the catalyst from leaking; and injecting hydrogen and a 200 g/L biobased sodium muconate solution into the microreactor, wherein a flow rate of a liquid is controlled by a constant-flux pump, a flow rate of the injected biobased sodium muconate solution is 0.1 mL/min, a gas flow rate is controlled by a gas flowmeter at 10 mL/min, and a pressure of hydrogen in the microreactor is 3 MPa, the microreactor requires a water/oil bath to maintain the reaction temperature, a reaction is conducted at 80° C., an inner diameter of the microreactor is ¼ inch, a height of a catalyst bed is 10 cm, a residence time is 157 s, and the reaction is conducted for 157 s;

the nickel-based hydrogenation catalyst is composed of carrier loaded metal nickel, wherein the average particle size of the metal nickel is 2.5-4.5 nm obtained by transmission electron microscopy (TEM), and the specific surface area of the nickel-based hydrogenation catalyst is 50-300 $m^2/g$; and the load of the metal nickel in the nickel-based hydrogenation catalyst is 2-40 wt %;

the biobased muconic acid is cis-muconic acid prepared from biomass raw material;

the biobased adipic acid is adipic acid converted from the biobased muconic acid.

2. The preparation method according to claim 1, wherein the nickel-based hydrogenation catalyst is filled into the micro packed bed reactor; the biobased muconic acid aqueous solution or the biobased sodium muconate aqueous solution and hydrogen are injected into the micro packed bed reactor; and the micro packed bed reactor is heated in a water bath or an oil bath to conduct a catalytic hydrogenation reaction to obtain adipic acid;

the microreaction device comprises a reaction liquid storage tank, a constant-flux pump, a micromixer, a micro packed bed reactor, a phase separator and a product collector connected successively; a hydrogen source is connected with the micromixer; a gas flow meter is arranged between the hydrogen source and the micromixer; a back pressure valve is arranged on the phase separator; the inner diameter of the micro packed bed reactor is 0.5-10 mm; and the length of the micro packed bed reactor is 2-20 cm; and the height of the filled catalyst bed is 2-15 cm.

3. The preparation method according to claim 1, wherein the preparation method comprises: conducting a hydrogenation reaction of the biobased sodium muconate aqueous solution to obtain a sodium adipate aqueous solution, dropwise adding inorganic acid for acidification, and then precipitating adipic acid solid by cooling.

\* \* \* \* \*